United States Patent [19]

Weigel

[11] Patent Number: 5,097,049

[45] Date of Patent: Mar. 17, 1992

[54] PROCESS AND INTERMEDIATES FOR CHIRAL EPOXIDES

[75] Inventor: Leland O. Weigel, Indianapolis, Ind.

[73] Assignee: Eli Lilly and Company, Indianapolis, Ind.

[21] Appl. No.: 518,384

[22] Filed: May 3, 1990

[51] Int. Cl.$^5$ ............................................. C07D 301/02
[52] U.S. Cl. .................... 549/539; 549/549; 549/561; 558/52; 560/149
[58] Field of Search ................ 549/539, 549, 561; 558/52; 560/149

[56] References Cited

U.S. PATENT DOCUMENTS 3,994,878  11/1976  Partridge, Jr. et al. ............ 549/561

FOREIGN PATENT DOCUMENTS 55-120575  9/1980  Japan ................................ 549/549

OTHER PUBLICATIONS

J. Am. Chem. Soc., Corey et al, vol. 102, No. 27, 1980, pp. 7984–7985.
Tetrahedron Letters, Pikul et al, vol. 28, No. 23, 1987, pp. 2627–2628.

*Primary Examiner*—C. Warren Ivy
*Assistant Examiner*—Ba K. Trinh
*Attorney, Agent, or Firm*—James J. Sales; Leroy Whitaker

[57] ABSTRACT

Chiral epoxybutyrates are prepared in high yield from novel dihydro-3R-substituted sulfonyloxy-4R-hydroxy-2-(3H)furanones via based catalyzed alcoholysis. The product chiral epoxy butyrates are useful intermediates for the synthesis of 1-carba-1-dethia cephem antibiotics.

2 Claims, No Drawings

PROCESS AND INTERMEDIATES FOR CHIRAL EPOXIDES

BACKGROUND AND SUMMARY OF THE INVENTION

This invention relates to a cost effective process for producing chiral intermediates useful in the synthesis of 1-(dethia)carbacephem antibiotics. More particularly, this invention is directed to the synthesis of chiral epoxybutyrates via novel dihydro-3R,4R-dihydroxy-2(3H)furanone 3-sulfonic acid esters.

The ability to introduce a chiral center is critical to the synthesis of many commercially significant biologically active compounds. When only one enantionmer is active, yield losses result not only from production of the inactive stereoisomer but also during separation and recovery of the desired product. In synthetic procedures involving multiple steps, low yielding steps, especially those early in the synthetic route, seriously affect the economics of the synthesis. Thus, there has been a continuing effort toward the development of chemistry relying on asymmetric induction to provide products of preferred stereochemical configuration. One particular area of such effort has been the stereoselective synthesis of β-lactam intermediates useful for the production of mono-bactams, clavulanic acid, thienamycin, and the 1-carba(1-dethia)cephalosporins. Among the more efficient methods for stereospecific construction of the β-lactam ring is the so-called ketene-imine cycloaddition comprising the reaction of an amino-protected glycyl chloride or other ketene generating derivative with an imine in the presence of a tertiary amine. For example, Evans et al., in U.S. Pat. No. 4,665,171 describe an asymmetric method for preparing the β-lactam ring which comprises a cyclo addition of an imine with a chiral 4-(S)-aryloxazolidin-2-on-3-yl-acetyl halide wherein the chiral aryl oxazolidinone functions to induce the desired chirality in the product azetidinones. A related method for synthesizing optically active β-lactams starting from optically active alpha-amino acids is described and claimed by Sugawara et al. in published European Application No. 144,840. Still another chiral synthesis of β-lactam intermediates is described in copending U.S. application Ser. No. 07/173,381, now allowed. That application describes a method for preparing β-lactam intermediates wherein the chirality of the β-lactam ring is induced with a chiral epoxy aldehyde employed to form the imine for use in a ketene-imine cycloaddition.

While each of those chiral syntheses offer the advantage of enhanced stereoselectivity, such advantages are offset by the expense of preparing the chirality inducing optically active intermediates. Thus, for example, the chiral epoxy aldehydes used to form the imine intermediates for cyclo addition with ketenes in accordance with the disclosure of Evans in the above referenced U.S. application Ser. No. 07/173,381 are, from a commercial perspective, not economically viable intermediates. Ongoing research and development efforts have been directed toward methods of synthesis of important chiral auxiliaries for the stereo selective production of β-lactam containing intermediates.

This invention provides a cost efficient synthesis of chiral 4-hydroxy-2,3-epoxybutyrate esters from novel, but readily available, chiral dihydro-3,4-dihydroxy-2(3H)furanone 2-sulfonic acid esters. The sulfonic acid ester intermediates are prepared in high yield from the corresponding dihydroxy furanones derived by peroxide oxidation of low cost isoascorbic acid or its sodium salt, sodium erythrobate. The chiral epoxybutyrate esters are oxidized in high yield using, for example, Swern oxidation conditions (oxalyl chloride, DMSO-triethylamine) to the corresponding chiral epoxy aldehydes which are key intermediates for the stereo selective synthesis of β-lactams in accordance with the above described method of Evans. The present method utilizing novel dihydro-3,4-dihydroxy-2(3H)furanone 3-sulfonic acid esters provides a cost effective method for preparing the important epoxy aldehyde β-lactam intermediates.

DETAILED DESCRIPTION OF THE INVENTION

This invention is directed to a method for preparing chiral epoxides of the formula

wherein R is the hydrocarbon residue of a $C_1$–$C_8$ alcohol. The chiral epoxides I are prepared in accordance with this invention by reacting novel intermediate γ-lactones of the formula

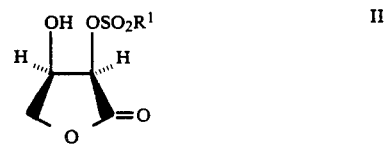

under substantially anhydrous conditions with at least one equivalent of an alkoxide of the formula $RO^-$ in the presence of an alcohol of the formula ROH wherein R is as defined above, and $R^1$ is $C_1$–$C_6$ alkyl, trifluoromethyl, benzyl, phenyl, tolyl or trimethylphenyl.

Representative of the hydrocarbon residues represented by the group R are $C_1$–$C_8$ alkyl, $C_3$–$C_8$ alkenyl and benzyl. The term "$C_1$–$C_8$ alkyl refers to methyl, ethyl, propyl, butyl, hexyl, octyl; methylcyclohexyl, isopropyl, isoamyl, and heptyl. "$C_2$–$C_8$ Alkenyl as used with reference to the present invention includes allyl, butenyl, including 2-butenyl, 3-butenyl, 2-methyl-2-butenyl and 2-ethyl-3-butenyl, 2-pentenyl, 3-pentenyl and 2-methyl-2-pentenyl; hexenyl including 2-hexenyl, 2-cyclohexenyl, 3-cyclohexenyl and 2,4-cyclohexyldienyl; 2-heptenyl, 3-methyl-3-heptenyl, 3-methyl-3-cyclohexenyl, 2-ethyl-3-cyclohexenyl and octenyl. The terms $C_1$–$C_8$ alkyl, $C_3$–$C_8$ alkenyl and benzyl as used in specifying in the present invention includes the corresponding substituted $C_1$–$C_8$ alkyl, substituted $C_3$–$C_8$ alkenyl and substituted benzyl groups wherein such groups are substituted with one or two substituents selected from the group consisting of halo, including chloro, bromo, and iodo, nitro, $C_1$–$C_4$ alkoxy, $C_1$–$C_4$ alkyl, trifluoromethyl, $C_1$–$C_4$ alkylthio, $C_1$–$C_4$ alkanoyloxy, carbamoyl, $C_1$–$C_4$ alkylsulfonylamino, $C_1$–$C_4$ alkanoylamino, and aminosulfonyl.

The term "$C_1$–$C_6$ alkyl" as used in defining $R^1$ in the above formula includes methyl, ethyl, n-propyl, isopropyl, butyl, isobutyl, amyl, hexyl, cyclohexyl, cyclopropyl, cyclopentyl, and 2-methylcyclopentyl.

The conversion of γ-lactone II to chiral epoxide I proceeds through an intermediate of the formula

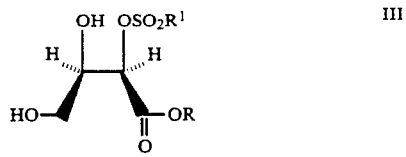

wherein R and R¹ are as defined above. Indeed, γ-lactone II is converted in nearly quantitative yield to ester III by alcoholysis using an alcohol of the formula ROH in the presence of an alkoxide or other alkoxide-forming base. The alcohol can be used as the reaction medium alone or in combination with an alcohol miscible inert organic solvent. The conversion of γ-lactone II to chiral ester III can be accomplished with a fractional equivalent of alkoxide-forming base in the presence of alcohol ROH. Thus, in accordance with a preferred embodiment of this invention, chiral epoxide I is prepared by reacting lactone II under substantially anhydrous conditions in the presence of an alcohol ROH, first with a fractional equivalent of an alkoxide or an alkoxide-forming base to convert γ-lactone II to chiral ester III and thereafter with the remaining portion of at least an equivalent of the alkoxide or alkoxide-forming base effective to complete conversion of ester intermediate III to chiral epoxide I.

Suitable alkoxide-forming bases within the meaning of that term as used in specifying the present invention are the salts of compounds less acidic than alcohols including metal hydrides such as sodium hydride and potassium hydride; alkyl or aryl lithium compounds such as n-butyllithium, phenyllithium, methyllithium, sodium naphthlylide, alkali metal amides such as lithium diisopropylamide, lithium hexamethyldisilazane and the like. Other "alkoxide-forming bases" for use in accordance with the present invention include alkoxides themselves, particularly alkali metal alkoxides of hindered alcohols such as tert-butyl alcohol or tertamyl alcohol. Preferably the "alkoxide-forming base" used for carrying out the method of this invention is the alkoxide RO⁻ corresponding to the alcohol ROH in the reaction mixture.

Complete conversion of lactone II to chiral epoxide I requires at least one equivalent of an alkoxide or alkoxide-forming base. Preferably about 1.0 to about 1.2 equivalents of the alkoxide-forming base is employed. The reaction is carried out in a substantially anhydrous reaction medium comprising a $C_1$-$C_8$ alcohol. Typically, the alcohol is present in excess of the amount corresponding to an equivalent of the starting lactone II. Thus, the reaction medium can comprise preferably from about 10 to about 200 equivalents of the alcohol per equivalent of lactone starting material II. Preferably, the reaction medium comprises an alcohol in combination with an alcohol miscible inert organic solvent to enhance the solubility of the lactone starting material in the reaction medium.

Suitable inert organic solvents are recognized polar aprotic solvents such as ethers, including tetrahydrofuran, dioxane, glyme, diglyme and like ethers; amides such as dimethylformamide and dimethylacetamide; and sulfoxido solvents such as dimethylsulfoxide (DMSO) and sulfolane.

The alcohols and inert solvents which comprise the reaction medium for carrying out the present method are ideally anhydrous or substantially anhydrous, meaning that such solvents are free of an amount of water which would materially interfere with the generation and use of the alkoxide reagent in accordance with this invention. Solvents processed using art recognized solvent drying techniques including azeotropic drying, distillation, molecular sieves and like techniques are suitable for use in accordance with this invention.

The conversion of lactone II to the chiral epoxybutyrates I in accordance with this invention is carried out by treating a solution of the lactone in an alcohol-containing reaction medium as described above with an alkoxide or alkoxide forming base at a temperature between about −60° and about 0° C., more preferably between about −30° and about −10° C. In accordance with a preferred embodiment of this invention a first portion of the alkoxide-forming reagent is added to the reaction mixture to effect conversion of the lactone II to ester intermediate III. The progress of the reaction can be followed using art recognized techniques such as thin layer chromatography (TLC) or high pressure liquid chromatography (HPLC). Conversion of the intermediate ester III to the chiral epoxybutyrate I is completed by adding the remainder of the alkoxide-forming base (preferably totalling between about 1.0 and about 1.2 equivalents of starting lactone II) to the reaction mixture at a temperature between about 0° C. and about −70° C., more preferably between about −10° and about −60° C. The product chiral epoxybutyrates I are isolated, typically in high yield, using standard reaction mixture workup and product purification procedures.

The novel chiral γ-lactone intermediates II used in the present method are prepared by selective sulfonation of the corresponding dihydro-3R,4R-dihydroxy-2(3H)furanone of the formula

prepared by alkaline hydrogen peroxide oxidation of isoascorbic acid or sodium erythrobate, an inexpensive and readily available $C_6$-carbohydrate (the epimer of L-ascorbic acid) as described by Cohen et al. in the *Journal of the American Chemical Society*, Vol. 105, No. 11, 1983 at pages 3663–3664. Dihydroxyfuranone IV is selectively sulfonated at the 3-hydroxy position with sulfonyl halides in the presence of a tertiary amine base to provide the novel lactone intermediates used in accordance with the method of this invention. Thus, the chiral dihydroxyfuranone IV can be sulfonated with a sulfonyl halide of the formula R¹SO₂Cl wherein R¹ is as defined above to provide the corresponding chiral 3-sulfonic acid esters II. Exemplary of sulfonyl halides useful in preparing novel lactone sulfonic acid ester II are methanesulfonyl chloride, cyclohexanesulfonyl chloride, trifluoromethonesulfonyl chloride, benzylsulfonyl chloride, benzenesulfonyl chloride, trimethylbenzenesulfonyl chloride and toluenesulfonyl chloride. Typically, the reaction is carried out at a temperature between about inert organic solvent as described above. The reaction is carried out at a temperature between about 25° C. and about −50° C., more preferably about 0° C. and about −30° C. The reaction is preferably carried out in the presence of a tertiary amine base comprising, for example, triethylamine, N,N-dimethylaniline, pyridine, or 4-dimethylaminopyridine, preferably in excess. Alternatively the reaction can be accomplished by reacting the chiral lactone diol in a dry aprotic polar solvent with a metal hydride, for example, sodium hydride, in the presence of an equivalent amount of a sulfonyl halide. The progress of the sulfonation can be followed by thin layer chromatography. The product sulfonic acid ester is isolated in high yield from the reaction mixture following standard reaction mixture workup procedure. The product can be purified by recrystallization or by use of other art-recognized purification techinques.

As mentioned above, the chiral epoxybutyrates I are useful intermediates for the synthesis of chiral β-lactam antibiotics, for example, the art-recognized 1-carba(1-dethia)cephalosporin compounds including particularly 7β-[2'-(R,S)-2'-phenyl-2'-aminoacetamido]-3-chloro-3-(1-carba-1-dethiacephem)-4-carboxylic acid (loracarbef). Thus, the chiral epoxybutyrates can be oxidized under Swern oxidation conditions to the corresponding epoxyaldehydes. The epoxyaldehydes are condensed with a glycine ester to provide the corresponding imine which reacts via cycloaddition with amino-protected glycyl halides in the presence of tertiary amine base to provide 3-protected-amino-4-(substituted oxiranyl) azetidinone intermediates which are converted to 1-carba-1-dethiacephems as described by Evans et al. in allowed copending application Ser. No. 07/173,381 filed Mar. 25, 1988 (published European Application No. 0334593, published Sept. 27, 1989.) The present invention provides a cost effective method and intermediates for synthesis of the critical chiral epoxide intermediates and thereby potentiates the commercial viability of chiral syntheses utilizing that intermediate.

The following Examples are provided to further exemplify preferred embodiments of the method and intermediate composition embodiments of the invention.

EXAMPLE 1

Dihydro-3R-[[(4-methylphenyl)sulfonyl]oxy]-4R-hydroxy-2(3H)furanone

A. A dry flask was charged with dihydro-3R,4R-dihydroxy-2(3H)furanone (1.18 g), acetone (20 ml), triethylamine (1.4 ml) and 4-dimethylaminopyridine (122 mg). The mixture was cooled (0° C., partial crystallization of furanone) and treated with p-toluenesulfonyl chloride (2.0 g). After 2 h at 0° C., the reaction mixture was poured into stirred ice water and filtered to provide 2.23 g (82%) of product (air dried at 25° C., 48 h). Analysis by TLC/$^1$H NMR/$^{13}$C NMR indicated that 10–13 mol-percent of 2-[[(4-methylphenyl)sulfonyl]oxy]-4-hydroxy-2-butenoic acid lactone was admixed with the titled product.

B. Dihydro-3R,4R-dihydroxy-2(3H)furanone (1.00 g) was dried by azeotropic distillation with pyridine (5 ml, 25° C., 1 mm), redissolved in 2.0 ml of dry pyridine and treated with p-toluenesulfonyl chloride (1.70 g, −30° C., 2.5 h). After 18 h, additional p-toluene-sulfonyl chloride (0.17 g) was added (−25° C.). The mixture was maintained at −25° C. for 48 h, quenched with 1 g of ice and thereafter poured onto 42.1 g of ice. Methanol (2 ml) was used for rinsing. Filtration (0°, rinse with water) and suction drying of the filtered product for 48 h afforded 2.21 g of the titled tosylate (96%) admixed with a small amount of the corresponding dihydro-3R-[[(4-methylphenyl)sulfonyl]oxy]-4R-hydroxy-2(3H)furanone Recrystallization of 1.86 g of that product mixture from tetrahydrofuran containing methylene chloride provided 1.37 g of the titled product.

$^{13}$C NMR (DMSO-d$_6$): δ 21.03, 67.06, 72.82, 75.09, 127.8, 130.00, 131.39, 145.28, 170.31, FD-MS m/z=272 (M$^+$, sole peak).

$[α]_D^{25}$ −49.7° (C=1, MeOH, qualitative since sample not entirely soluble).

TLC Rf (ethyl acetate-hexane, 1:1): 0.41.
Analysis calculated for C$_{11}$H$_{12}$O$_6$S:
Calc.: C, 48.53; H, 4.44; S, 11.77;
Found: C, 48.55; H, 4.74; S, 12.04.

EXAMPLE 2

Dihydro-3R-methanesulfonyloxy-4R-hydroxy-2(3H)furanone

To a solution/suspension of dihydro-3R,4R-dihydroxy-2(3H)furanone (7.5 g) in 45 ml of pyridine was added methane sulfonyl chloride (8.0 g) with stirring at ambient temperature.

The course of the reaction was followed by TLC (2:1/ethylacetate:hexane), and upon disappearance of the starting material, the reaction mixture was poured onto ice. Filtration of the resulting aqueous provided 8.44 g (air dried) of the titled product.

EXAMPLE 3

Methyl 4-hydroxy-2S,3R-epoxybutyrate

A. To a solution of 10 g of the tosylate prepared in accordance with Example 1 in tetrahydrofuranmethanol (1:4, 150 ml, −10° to −25° C.) was added sodium methoxide (25% w/v in methanol, 0.5 ml initially, then 7.5 ml in portions over 4 h). After 24 h at −20° C., 5 g of solid carbon dioxide was added, and the pH was adjusted to 7.2 with 1N sulfuric acid. The mixture was concentrated in vacuo. Ethyl acetate (250 ml) and sodium sulfate (10 g) were added, and after 24 h, hexane (100 ml) was added and the mixture was filtered through silica gel (100 g) using ethyl acetate-hexane (2:1) as eluent. Evaporation of product-containing fractions afforded 4.88 g (91%) of the titled methyl ester.

$^{13}$C(CDCl$_3$): δ 6 50.07, 52.59, 58.00, 60.08, 169.41.
$[α]_D^{25}$ = +37.45°, 36.97°, (C=1, methanol); +30.94° (C=1, acetone); +32.63° (C=1, chloroform); +35.07° (C=1, pyridine)

$^1$H NMR (Methanol-d$_4$): δ 3.74 (s, 3H), 3.50 (d, 1H). (Acetone, d$_6$) δ 3.83 (s, 3H), 3.43 (d, 1H). (Chloroform-d$_1$): δ 3.80 (s, 3H), 3.55 (d, 1H), 2.37 (broad, 1H). (Toluene-d$_8$): δ 3.27 (s, 3H), 3.17 (d, 1H), 0.81 (d×d, 1H).

Analysis calculated for C$_5$H$_8$O$_4$:
Calc.: C, 45.46; H, 6.10;
Found: C, 45.20; H, 5.86.

B. A mixture of dihydro-3R,4R-dihydroxy-2(3H)furanone (2.00 g), dimethylsulfoxide (5 ml), 4-A molecular sieves (7 g) sodium bicarbonate (1 g), and tetrahydrofuran (10 ml) was stirred for 2 h at 25° C. The solution was filtered, cooled (0° C.) treated with p-toluenesulfonyl chloride (1.05 equivalent in 30 ml of tetrahydrofuran), and thereafter sodium hydride (0.68 g, 60% oil dispersion). After 90 minutes the reaction was sequentially treated with dry methanol (250 ml), catalytic sodium methoxide (5 drops at 25% w/v 5 min), then sodium methoxide (1 equiv. 25% w/v in methanol). Quenching (acetic acid, pH 7) of the reaction mixture and chromatography over silica gel as described in paragraph A above afforded 1.41 g (63%) of the titled methyl ester.

EXAMPLE 4

Ethyl 4-hydroxy-2S,3R-epoxybutyrate

Dihydro-3R,4R-dihydroxy-2(3H)furanone was prepared according to the method of Cohen et al., J. Am. Chem. Soc., Vol 105, No. 11, 3361 (1983)], extracted into ethyl acetate, neutralized, (solid sodium bicarbonate), and dried (4A molecular sieves). A 100-ml aliquot of the solution (titer=1.02 g/100 ml) was treated with 4-dimethylaminopyridine (87 mg), triethylamine (1.62 ml), 1.77 g of p-toluenesulfonyl chloride (20°-25° C., 6 h), and a second portion of p-toluenesulfonyl chloride (0.10 g; 24 h). Extractive workup [water (100 ml), 0.1N HCl (2×50 ml), brine (50 ml) and sodium sulfate] provided 90 ml of a solution of dihydro-3R-[[(4-methylphenyl)-sulfonyl]oxy]−4R-hydroxy-2(3H)furanone. An 81 ml portion of that solution was concentrated in vacuo to about 10–30 ml. Ethanol (50 ml) was added and the mixture was concentrated in vacuo. After repeating that procedure three times, tetrahydrofuran (30 ml) was added followed by sodium ethoxide (1.0 equivalent in 27 ml of ethanol, −28° C., 4 h). The reaction mixture was quenched (carbon dioxideacetic acid, pH=7) and evaporated in vacuo. Filtration through silica gel (20 g, hexane-ethyl acetate 40:1 varied to 2:1) and evaporation of the product-containing filtrate afforded the epoxide (1.14 g, 81% from the dihydrodihydroxyfuranone).

IR (CHCl$_3$): 3597 (Sh, OH), 3400 (broad), 1744 cm$^{-1}$.

$^1$NMR (CDCl$_3$): δ 4.23 (2H, m), 3.98 (1H, d×d), 3.75 (1H, d×d), 3.52 (1H, d), 3.98 (1H, m), 2.55 (1H, broad, exchanges with D$_2$O), 1.33 (3H, t).

$^{13}$C (CDCl$_3$): δ 14.46, 50.58, 58.36, 60.49, 62.19, 169.38.

Analysis calculated for C$_6$H$_{10}$O$_4$:
Calc.: C, 49.31; H, 6.90;
Found: C, 49.18; H, 6.65.

EXAMPLE 5

Benzyl 4-hydroxy-2S,3R-epoxybutyrate

A mixture of dihydro-3R-[[(4-methylphenyl)sulfonyl]oxy]-4R-hydroxy-2(3H)furanone (31.5 g), tetrahydrofuran (500 ml) and benzyl alcohol (312.0 g) was degassed (vacuum-N$_2$) and dried (4h; 4-A molecular sieves, 25° C.). The solution was separated via cannula from the molecular sieves, cooled to −25° C., and treated with 0.50 g of sodium hydride (60% oil dispersion). The progress of the reaction was monitored by TLC. After disappearance of the starting material (TLC, R$_f$=0.46, silica gel ether-pentane, 3:1), an additional portion of THF (250 ml) and sodium hydride (4.22 g, 60% oil dispersion were added (−45° C. to −60° C.).

After 18 h at −20° to −30° C., the reaction mixture was treated with solid carbon dioxide (10 g), ether (1L), pH 7 phosphate buffer (0.5L, pH=6.9), and solid sodium chloride (saturation of aqueous phase). The aqueous phase was separated and re-extracted with ether (200 ml). Evaporation of the combined, dried (sodium sulfate) organic extracts afforded 325.6 g of a mixture of benzyl alcohol and the titled benzyl ester. Chromatography of a 32 g portion of this mixture (Waters Prep ® 500, silical gel with hexane-ethyl acetate, 2:1 varied to 1:1) provided the titled product which crystallized from ether-hexane:mp 39°-42° C.

$^{13}$C NMR (CDCl$_3$): δ 50.16, 58.07, 60.04, 67.38, 128.48, 128.63, 128.63, 135.00, 168.84

$^1$H NMR (CDCl$_3$): δ 7.38 (s, 5H), 5.18 (d×d, 2H), 3.58 (d, 1H), 2.53 (d×d, 1H).

Analysis calculated for C$_{11}$H$_{12}$O$_4$:
Calc.: C, 63.45; H, 5.81;
Found: C, 63.23; H, 5.73.

EXAMPLE 6

Allyl 4-hydroxy-2S,3R-epoxybutyrate

Dry dihydro-3R-[[(4-methylphenyl)sulfonyl]oxy]-4R-hydroxy-2(3H)furanone (2.30 g) was dissolved in allyl alcohol (58 g) and tetrahydrofuran (50 ml) and cooled to −20° C. (partial crystallization). With good stirring, 3.00 ml of sodium allyloxide (0.124M in allyl alcohol-tetrahydrofuran, 56:371, w/w) was added at −20° C. over 1 hour. Thereafter, an additional 65.2 ml of the sodium allyl oxide solution was added (−10° C. to −20° C.). The reaction mixture was allowed to stand 18 h at −20° C., quenched with acetic acid (pH=7.0), and evaporated in vacuo. Filtration of the ethyl acetate soluble residue over silica gel (15 g, sequential washing with 50 ml of dichloromethane; 50 ml of 4:1 hexane-ether; 120 ml of 1:1 ethyl acetate-hexane) and evaporation of the product-containing filtrate afforded the titled allyl ester.

[α]$_D^{23°}$= +27.4° (c=1, chloroform)
[α]$_D$= +24.6° (c=1, methanol).

$^1$H NMR (CDCl$_3$): δ 5.91 (1H, m, —C$\underline{H}$=), 5.30 (2H, m, C=CH$_2$), 4.68 (2H, m), 4.00 (1H, d×d), 3.77 (1H d×d) 3.58 (1H, d), 3.42 (1H, m), 1.97 (1H, broad, —O$\underline{H}$).

IR (CHCl$_3$): 3603 (sharp, nonhydrogen bonded OH), 1748, 1197 cm$^{-1}$ $^{13}$C (CDCl$_3$): δ 50.11, 57.9, 60.07, 66.24, 119.31, 131.33, 168.52.

EXAMPLE 7

Isoamyl 4-hydroxy-2S,3R-epoxybutyrate

A 3-L flask was charged with dihydro-3R-[[(4-methylphenyl)sulfonyl]oxy]−4-hydroxy-2(3H)furanone (20.0 g), isoamyl alcohol (332 g), and tetrahydrofuran (539 g). This solution was cooled (−9° C. to −17° C.) and a solution of sodium isomaylate (0.34M, 205 ml) was added over 4.5 hours. After 3.5 hours (−17° C.), the reaction mixture was treated with 0.5 ml of acetic acid and 0.5 g of sodium bicarbonate. The mixture was washed with brine (3×100 to 150-ml portions) and concentrated in vacuo. Filtration through silica gel with ethylacetate-hexane (1:4 varied to 2:5) and evaporation of the product-containing filtrate afforded 12.64 g (92%) of the titled product.

TLC R$_f$(ethyl acetate-hexane, 1:1) 0.40.

$^1$H NMR (CDCl$_3$): δ 4.21 (m, 2H), 3.97 (d×d, 1H), 3.74 (1H, d×d), 3.47 (1H, d), 3.38 (1H, m), 2.58 (1H, D$_2$O exchanges), 1.79 (1H, m) 1.57 (2H, q), 0.98 (6H, d).

$^{13}$C (CDCl$_3$): δ 22,51, 25.08, 37.21, 50.29, 58.08, 60.22, 64.56, 169.18.

[α]$_D^{25°}$ +22.45° (C=1 methanol).
MS (FD) m/z 189 (M$^+$+1), 155.
IR (CHCl$_3$) 3500 (broad), 1743 cm$^{-1}$.

I claim:

1. A method of preparing a compound of the formula

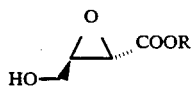

which method comprises reacting a compound of the formula

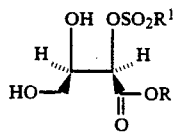

wherein said compound of formula 2 is generated in situ by base catalyzed alcoholysis of a lactone of the formula

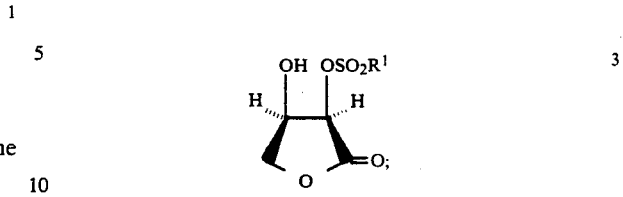

with at least one equivalent of an alkoxide-forming base in a substantially anhydrous reaction medium comprising a $C_1$–$C_8$ alcohol wherein R is the hydrocarbon residue of a $C_1$–$C_8$ alcohol and $R^1$ is $C_1$–$C_6$ alkyl, trifluoromethyl, benzyl, phenyl or tolyl.

2. The method of claim 1 where R is $C_1$–$C_8$ alkyl, $C_3$–$C_8$ alkenyl or benzyl.

* * * * *